United States Patent [19]
Santalucia et al.

[11] Patent Number: 5,939,051
[45] Date of Patent: Aug. 17, 1999

[54] DENTAL ABRASIVE

[75] Inventors: John Santalucia, New Brunswick; Peter Ren, Martinsville; Nagaraj Dixit, Plainsboro; Gary Durga, Edison; Michael Prencipe, Princeton Junction; Mahmoud Hassan, Piscataway; Marcus Bentley, Jersey City; Barry Self, Somerset, all of N.J.

[73] Assignee: Colgate-Palmolive Company, New York, N.Y.

[21] Appl. No.: 09/031,727

[22] Filed: Feb. 27, 1998

[51] Int. Cl.[6] .................. A61K 7/16; A61K 7/18
[52] U.S. Cl. ............. 424/49; 424/52; 423/335; 423/339
[58] Field of Search .............. 424/49–58; 423/335, 423/339

[56] References Cited

U.S. PATENT DOCUMENTS

| | | | |
|---|---|---|---|
| 3,980,767 | 9/1976 | Chown et al. . | |
| 4,153,680 | 5/1979 | Seybert . | |
| 4,303,641 | 12/1981 | DeWolf et al. | 424/49 |
| 4,328,205 | 5/1982 | Taylor . | |
| 4,340,583 | 7/1982 | Wason . | |
| 4,346,071 | 8/1982 | Dent et al. | 424/49 |
| 4,358,437 | 11/1982 | Duke . | |
| 4,420,312 | 12/1983 | Wason . | |
| 4,421,527 | 12/1983 | Wason . | |
| 4,474,824 | 10/1984 | DeWolf et al. | 424/49 |
| 4,485,089 | 11/1984 | Leipold | 424/49 |
| 4,632,628 | 12/1986 | Plöger et al. . | |
| 4,726,943 | 2/1988 | Klueppel et al. | 424/49 |
| 4,943,429 | 7/1990 | Winston et al. . | |
| 5,176,899 | 1/1993 | Montgomery . | |
| 5,270,033 | 12/1993 | Montgomery . | |
| 5,589,160 | 12/1996 | Rice | 424/49 |
| 5,603,920 | 2/1997 | Rice | 424/49 |
| 5,651,958 | 7/1997 | Rice . | |
| 5,658,553 | 8/1997 | Rice . | |
| 5,676,932 | 10/1997 | Wason et al. | 424/49 |
| 5,716,601 | 2/1998 | Rice . | |
| 5,747,008 | 5/1998 | Wason et al. | 424/49 |

FOREIGN PATENT DOCUMENTS 2038303  7/1980  United Kingdom .

*Primary Examiner*—Shep K. Rose
*Attorney, Agent, or Firm*—Henry S. Goldfine

[57] ABSTRACT

Oral compositions, such as oral gels and toothpastes, containing a novel high cleaning, low abrasion silica hydrogel abrasive.

10 Claims, No Drawings

DENTAL ABRASIVE

FIELD OF THE INVENTION

This invention relates to dentifrice compositions containing a silica abrasive, which provide improved oral cleaning with low abrasivity.

BACKGROUND OF THE INVENTION

Synthetically produced silicas play an important role as an ingredient in many of today's toothpaste formulations. Such silicas are relatively safe, nontoxic, ingredients which are compatible with other toothpaste ingredients, including glycerin, sorbitol (or xylitol), thickening agents, detergents, coloring and fragrance materials and optionally fluoride and other actives. Further, silicas act as an abrasive to clean teeth, remove plaque and food debris.

As an abrasive or polishing agent, silicas debride and physically scrub the external surface of the teeth. This scrubbing action removes the organic film (i.e. the pellicle), formed of salivary proteins which covers the teeth and which is known to become stained and discolored by foods, such as coffee, tea and berries, as well as, by tobacco smoke, cationic antibacterials, and chromogenic bacteria. Such physical removal of the stained pellicle is a simple and effective means of removing the undesirable surface staining and discoloration which occurs daily. Further, such physical removal of the pellicle also removes plaque bacteria on the pellicle surface.

Synthetic silicas include both silica gels and precipitated silicas which are prepared by the neutralization of aqueous silicate solutions with a strong mineral acid. In the preparation of silica gel, a silica hydrogel is formed which is then typically washed to low salt content. The washed hydrogel may be milled to the desired size, or otherwise dried, ultimately to the point where its structure no longer changes as a result of shrinkage. When preparing such synthetic silicas, the objective is to obtain abrasives which provide maximal cleaning (i.e. removal of stained pellicle) with minimal damage to the tooth enamel and other oral tissue. Dental researchers are continually concerned with identifying synthetic silicas meeting these objectives.

U.S. Pat. No. 4,153,680 and GB Patent Application 2,038,303A both disclose the general use of silica hydrogels or hydrated silica gels as dentifrice polishing agents. U.S. Pat. No. 4,632,826 discloses the use of hydrated silica gels in combination with a weakly calcined alumina polish, to form a combination abrasive system. U.S. Pat. Nos. 4,943,429, 5,176,899 and 5,270,033 provide lists of alternative polishing agents, such lists including hydrated silica gels.

In spite of the disclosures relating to silica hydrogels and other compositions for oral cleaning, there is still a need for additional compositions providing improved pellicle cleaning, improved removal of plaque and food debris, all with minimal abrasion of the tooth enamel and other oral tissue.

SUMMARY OF THE INVENTION

The present invention relates to dentifrice compositions, comprising:
(a) an orally acceptable dentifrice vehicle from about 5% to about 95% by weight of the dentifrice composition; and
(b) a silica hydrogel of from about 3% to about 30% of the dentifrice composition, containing from 10% to 25% water by weight, wherein:
  (i) the silica hydrogel is composed of particles of from about 2 to about 4 microns, the particles having the properties:
  (ii) a Brunauer, Emmett and Teller (BET) surface are in the range of 150 to 400 $m^2/g$ of silica;
  (iii) an oil absorption of less than 100 $cm^3/100$ g silica; and
  (iv) a pH, in a 5% w/w suspension in boiled ($CO_2$ free) demineralized water, equal to or greater than 8.5; and
wherein, the dentifrice composition has a radioactive dentin abrasion (RDA) of from 90 to 250, preferably from about 95 to about 160, and a pellicle cleaning ratio (PCR) from about 70 to about 130.

Surprisingly, while in general silica gels have been reported as having acidic pH levels (Morton Pader, *Oral Hygiene Products and Practice*, pages 254–255, Marcel Dekker, Inc., New York {1988}) and silica hydrogels (i.e. hydrous silica gels) of smaller micron size and higher pH levels have been reported as having unacceptably low abrasion values (GB 2,038,303A, Table 4, page 9); the silica hydrogel of the present invention, which has a pH of at least 8.5, exhibits commercially acceptable RDA abrasion values of at least 90.

Details of the above physical measurements and attributes are discussed below. All measurement levels and ratios are by weight of the total composition, unless otherwise indicated, such as the case of Pellicle Cleaning Ratio (PCR) and Radioactive Dentin Abrasion (RDA) values, which are unitless. Additionally, all measurements are made at 25° C., unless otherwise specified.

DETAILED DESCRIPTION OF THE INVENTION

By "dentifrice composition," as used herein, means a toothpaste, tooth powder, prophylaxis paste, lozenge, gum, or oral gel.

By the term "orally-acceptable dentifrice vehicle," as used herein, means a suitable carrier which can be used to apply the present compositions to the oral cavity in a safe and effective manner. The orally-acceptable vehicle as well as the other essential and optional components of the compositions of the present invention are described in the following paragraphs.

Abrasive

The silicas hydrogel or hydrous silica gel forming the silica compositions of the present invention are colloidal particles of silica linked together within a three-dimensional network, which can be characterized as a low density silica gel (such as an aerogel), having a larger pore volume (up to about 4 cc/g), cf., *Kirk-Othmer's Encyclopedia of Chemical Technology*, Vol. 21, pages 1020–1021, John Wiley & Sons, New York ($4^{th}$ Edition 1997). Such silicas are preferably characterized as synthetic hydrated amorphous silicas, also known as silicon dioxides or $SiO_2$. Further, these silicas may be characterized as having a surface area as characterized by the standard nitrogen absorption method of Brunauer, Emmett and Teller (BET) in the range of 150–400 $m^2/g$. Surface area is determined by the BET nitrogen adsorption method as described in Brunauer et al., J. Am. Chem. Soc., 60, 309 (1938). The BET measurement is preformed using an Accelerated Surface Area and Porosimetry Analyzer (ASAP 2400), by Micromeritics Instrument Corporation, Norcross, Ga. 30093. The sample is outgassed under vacuum at 350° C. for a minimum of 2 hours before measurement.

The silica hydrogel compositions of the present invention are further characterized as having a low average particle size ranging from about 2 micron to about 4 microns with a standard deviation of less than about 0.5 microns. The average particle size is measured using a Malvern Particle Size Analyzer, Model Mastersizer S, Malvern Instruments, Inc., Southborough, Mass. 01772. Specifically, a helium-neon gas laser beam is projected through a transparent cell which contains the silica hydrogel particles suspended in an aqueous solution. Light rays which strike the particles are scattered through angles which are inversely proportional to the particle size. The photodetector array measures the quantity of light at several predetermined angles. Electrical signals proportional to the measured light flux values are then processed by a microcomputer system, against a scatter pattern predicted from theoretical particles as defined by the refractive indices of the sample and aqueous dispersant to determine the particle size distribution of the silica hydrogel.

The silica hydrogel used to form the compositions of the present invention are further differentiated by means of their oil absorption values, having oil absorption values of less than 100 cc/100 g, and preferably in the range of from 45 cc/100 g silica to 90 cc/100 g silica. Oil absorption values are measured by determining the quantity of dibutyl phthalate oil absorbed in a fixed quantity of silica, when the oil-silica mixture reaches a maximum viscosity. Using a constant rate buret, the oil is added to a measured quantity of silica, in grams, in a mixing chamber linked to a torque rheometer, such as a Brabender Electronic Plasti-Corder Torque Rheometer, available from C.W. Brabender Instruments, Inc., South Hackensack, N.J. 07606. The volume of oil added at the maximum viscosity is input into the following equation:

$$\text{Oil absorption in cc/g of silica} = \text{quantity of oil in cc} \times 100 / \text{wt. of silica sample in grams}$$

wherein the quantity of oil is the time of addition of the oil in seconds times the buret delivery rate of the oil in cc/second.

Preparation of the silica hydrogels of the present invention is known in the art, for example, in U.S. Pat. No. 4,153,680 and U.K. Patent Application GB 2,038,303A, the hydrous silica gels being the result of the reaction of an alkali silicate solution with an $SiO_2$ concentration of about 6 to 20 percent by weight in the presence of a mineral acid, such as sulfuric acid, hydrochloric acid, nitric acid, or phosphoric acid. Sodium or potassium silicate may be used as the alkali silicate, with sodium silicate being preferred. A less than stoichiometric amount of acid is added to the alkali silicate solution until a pH of less than 10 to 11 is reached, a pH of about 8.5 being preferred. The resulting product is a solid silica which includes the water within its pores. After the silica hydrogel is formed it is washed with an alkali pH solution of pH at least 8.5, to maintain the high pH of the silica gel, at low temperatures of from about 0 to 60° C., until a purity level of about 98% $SiO_2$ is obtained (the remaining impurity being sodium sulphate). The resulting silica hydrogel is milled to the desired 2 to 4 microns in diameter particle size and dried to a water content of from 10 to 25% by weight, preferably about 20% by weight, to yield the desired silica hydrogel.

A preferred silica hydrogel abrasive of the present invention is marketed under the trade designation Sylodent XWA300 by Davison Chemical Division of W.R. Grace & Co., Baltimore, Md. 21203. The Sylodent XWA300 silica hydrogel is composed of particles of colloidal silica averaging from about 2 to about 4 microns in diameter, having a BET surface area of from 100 to 200 $m^2/g$ of silica, an oil absorption of less than 100 $cm^3/100$ g of silica and a pH greater than 8.5. Commercially available abrasives which may be used in combination with the silica hydrogel, include silicas having a mean particle size of up to about 20 microns, such as Zeodent 115, marketed by J.M. Huber Chemicals Division, Havre de Grace, Md. 21078, or Sylodent 783 also marketed by Davison Chemical Division of W.R. Grace & Co.

The abrasivity of the dentifrice compositions of the present invention, containing the silica hydrogel abrasives described herein, can be determined by means of RDA values as determined according to the method recommended by the American Dental Association, set forth by Hefferren, Journal of Dental Research, Volume 55, Issue 4, July-August 1976, pp. 563–573, and described in the Wason U.S. Pat. Nos. 4,340,583, 4,420,312 and 4,421,527. In this procedure extracted human teeth are irradiated with a neutron flux and subjected to a standard brushing regime. The radioactive phosphorus 32 removed from the dentin in the roots is used as the index of the abrasion of the dentifrice tested. A reference slurry containing 10 grams of calcium pyrophosphate in 15 ml of 0.5% aqueous solution of sodium carboxymethyl cellulose is also measured and the RDA of this mixture is arbitrarily taken as 100. The silica hydrogel dentifrice to be tested is prepared as a suspension at the same concentration as the pyrophosphate and submitted to the same brushing regime. The RDA of the silica hydrogel abrasive dentifrice of the present invention is from 250 to 90, preferably from about 160 to about 95.

The Pellicle Cleaning Ratio (PCR) of the silica hyrogel compositions of the present invention, a measurement of the cleaning characteristics of dentifrices, generally ranges from about 70 to 130 and is preferably greater than about 95.

The PCR (Pellicle Cleaning Ratio) cleaning values are determined by a PCR test generally described in "In Vitro Removal of Stain With Dentifrice", G. K. Stookey et al., J. Dental Research, Vol. 61, pages 1236–9, November 1982. Cleaning is assessed in vitro by staining 10 $mm^2$ bovine enamel specimens embedded in resin, which are acid etched to expedite stain accumulation and adherence. The staining is with a broth prepared from instant coffee, instant tea and finely ground gastic mucin dissolved into a sterilized trypticase soy broth containing a 24-hour Sarcina lutea turtox culture. After staining, the specimens are mounted on a V-8 cross-brushing machine equipped with soft nylon toothbrushes adjusted to 150 g tension on the enamel surface. The specimens are then brushed with the dentifrice of the present invention and a calcium pyrophosphate standard (10 grams of calcium pyrophosphate in 50 ml of 0.5% aqueous solution of sodium carboxymethyl cellulose). The specimens are brushed with dentifrice slurries consisting of 25 g of toothpaste in 40 g of deionized water, for 400 strokes. The specimens are cleaned with Pennwalt pumice flour until the stain is removed. Reflectance measurements are taken using a Minolta Chromameter; wherein a Commission Internationale de l'Eclairage (CIE) L* a* b* scale is used to measure the color of the specimens.

The percent stain (SR) removed is calculated using the following formula:

$$\%SR = ((L_2^* - L_1^*)^2 + (a_2^* - a_1^*)^2 + (b_2^* - b_1^*)^2)^{0.5} \times 100 / ((L_3^* - L_1^*)^2 + (a_3^* - a_1^*)^2 + (b_3^* - b_1^*)^2)^{0.5}$$

wherein: $L_1^*$, $a_1^*$, and $b_1^*$, are reflectance measurements taken before brushing, $L_2^*$, $a_2^*$, and $b_2^*$ are reflectance readings taken after brushing, and $L_3^*$, $a_3^*$, and $b_3^*$ are measurements taken after pumacing.

The pellicle cleaning ratio is measured as follows:
PCR=% SR for Sample/% SR for Calcium Pyrophosphate Standard×100

The silica hydrogel abrasive can be present as the sole abrasive within the dentifrice compositions of the present invention or in combination with other known dentifrice abrasives or polishing agents. Other useful dentifrice abrasives include sodium metaphosphate, potassium metaphosphate, tricalcium phosphate, dihydrated dicalcium phosphate, aluminum silicate, calcined alumina, bentonite or other siliceous materials, or combinations thereof.

The total quantity of abrasive within the present invention is at a level of from about 5% to about 30% by weight, preferably from about 8% to about 12% by weight when the dentifrice composition is a toothpaste. Higher levels, as high as 95%, may be used if the dentifrice composition is a toothpowder.

Dentifrice Vehicle

The orally-acceptable dentifrice vehicle used to prepare the dentifrice composition comprises a water-phase, containing a humectant therein. The humectant is preferably glycerin, sorbitol, xylitol, and/or propylene glycol of molecular weight in the range of 200–1,000; but, other humectants and mixtures thereof may also be employed. The humectant concentration typically totals about 5 to about 70% by weight of the oral composition.

Reference hereto to sorbitol refers to the material typically commercially available as a 70% aqueous solution. Water is present typically in amount of at least about 10% by weight, and generally about 25 to 70% by weight of the oral composition. Water employed in the preparation of commercially suitable toothpastes should preferably be deionized and free of organic impurities. These amounts of water include the free water which is added plus that which is introduced with other materials such as with sorbitol.

The dentifrice compositions of the present invention and can contain a variety of optional dentifrice ingredients. As described below, such optional ingredients can include, but are not limited to, thickening or gelling agents, surfactants (i.e. surface acting agents), a source of fluoride ions, a synthetic anionic polycarboxylate, a flavoring agent, additional antiplaque agents and/or abrasives, and coloring agents.

Thickening Agents

Thickeners used in the compositions of the present invention include natural and synthetic gums and colloids, examples of which include carrageenan (Irish moss), xanthan gum and sodium carboxymethyl cellulose, starch, polyvinylpyrrolidone, hydroxyethylpropyl cellulose, hydroxybutyl methyl cellulose, hydroxypropylmethyl cellulose, and hydroxyethyl cellulose. Inorganic thickeners include amorphous silica compounds which function as thickening agents and include colloidal silicas compounds available under trademarks such as Cab-o-sil fumed silica manufactured by Cabot Corporation and distributed by Lenape Chemical, Bound Brook, N.J.; Zeodent 165 from J.M. Huber Chemicals Division, Havre de Grace, Md. 21078; and Sylox 15, also known as Sylodent 15, available from Davison Chemical Division of W.R. Grace Corporation, Baltimore, Md. 21203. The thickening agent is present in the dentifrice composition in amounts of about 0.1 to about 10% by weight, preferably about 0.5 to about 4% by weight.

Surfactants

Surfactants are used in the compositions of the present invention to achieve increased prophylactic action and render the dentifrice compositions more cosmetically acceptable. The surfactant is preferably a detersive material which imparts to the composition detersive and foaming properties. Suitable examples of surfactants are water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkyl sulfoacetates, sodium lauryl sulfoacetate, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl, or N-palmitoyl sarcosine. The surfactant is typically present in the dentifrice compositions of the present invention in an amount of about 0.3 to about 5% by weight, preferably about 0.5 to about 2% by weight.

Fluoride and Other Active Agents

The dentifrice composition of the present invention may also contain a source of fluoride ions or fluorine-providing component, as anticaries agent in amount sufficient to supply about 25 ppm to 5,000 ppm of fluoride ions and include inorganic fluoride salts, such as soluble alkali metal salts, for example, sodium fluoride, potassium fluoride, sodium fluorosilicate, ammonium fluorosilicate, sodium monofluorophosphate, as well as tin fluorides, such as stannous fluoride and stannous chloride. Sodium fluoride is preferred.

In addition to fluoride compounds, there may also be included antitartar agents such as pyrophosphate salts including dialkali or tetraalkali metal pyrophosphate salts such as $Na_4P_2O_7$, $K_4P_2O_7$, $Na_2K_2P_2O_7$, $Na_2H_2P_2O_7$ and $K_2H_2P_2O_7$ long chain polyphosphates such as sodium hexametaphosphate and cyclic phosphates such as sodium trimetaphosphate. These antitartar agents are included in the dentifrice composition at a concentration of about 1 to about 5% by weight. Another active agent useful in dentifrice compositions of the present invention are antibacterial agents, which can be from 0.2 to 1.0% by weight of the dentifrice composition. Such useful antibacterial agents include non-cationic antibacterial agents which are based on phenolic or bisphenolic compounds, such as halogenated diphenyl ethers like triclosan (2,4,4'-trichloro-2'-hydroxydiphenyl ether), benzoate esters or carbanilides. A preferred antibacterial agent is triclosan, which is a broad-spectrum antibacterial agent, marketed for use in oral products under the trademarks Irgacare MP or Irgasan DP300 by Ciba-Geigy Corporation, Greensboro, N.C. 27419.

Anionic Polycarboxylate

Synthetic anionic polycarboxylates may also be used in the dentifrice compositions of the present invention as an efficacy enhancing agent for any antibacterial, antitartar or other active agent within the dentifrice composition. Such anionic polycarboxylates are generally employed in the form of their free acids or preferably partially or more preferably fully neutralized water soluble alkali metal (e.g. potassium and preferably sodium) or ammonium salts. Preferred are 1:4 to 4:1 copolymers of maleic anhydride or acid with another polymerizable ethylenically unsaturated monomer, preferably methylvinylether/maleic anhydride having a molecular weight (M.W.) of about 30,000 to about 1,800,000 most preferably about 30,000 to about 700,000. Exemplars of these copolymers are available from GAF Corporation under the tradename Gantrez, e.g. AN 139 (M.W.

500,000), AN 119 (M.W. 250,000); S-97 Pharmaceutical Grade (M.W. 700,000), AN 169 (M.W. 1,200,000–1,800, 000), and AN 179 (M.W. above 1,800,000); wherein the preferred copolymer is S-97 Pharmaceutical Grade (M.W. 700,000).

When present, the anionic polycarboxylates is employed in amounts effective to achieve the desired enhancement of the efficacy of any antibacterial, antitartar or other active agent within the dentifrice composition. Generally, the anionic polycarboxylates is present within the dentifrice composition from about 0.05% to about 4% by weight, preferably from about 0.5% to about 2.5% by weight.

Flavor

The dentifrice composition of the present invention may also contain a flavoring agent. Flavoring agents which are used in the practice of the present invention include essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Of these, the most commonly employed are the oils of peppermint and spearmint.

The flavoring agent is incorporated in the dentifrice composition at a concentration of about 0.1 to about 5% by weight and preferably about 0.5 to about 1.5% by weight.

Other Ingredients

Various other materials may be incorporated in the dentifrice compositions of this invention, including desensitizers, such as potassium nitrate; whitening agents, such as hydrogen peroxide, calcium peroxide and urea peroxide; preservatives; silicones; and chlorophyll compounds. These additives, when present, are incorporated in the dentifrice composition in amounts which do not substantially adversely affect the properties and characteristics desired.

Preparation Of The Dentifrice

The preparation of dentifrices is well known in the art, such as described in U.S. Pat. Nos. 3,996,863, 3,980,767, 4,328,205 and 4,358,437, which are incorporated herein by reference. More specifically, to prepare a dentifrice of the present invention, generally the humectants e.g. glycerin, sorbitol, propylene glycol, and polyethylene glycol; are dispersed in the water in a conventional mixer under agitation. Into the dispersion are added the organic thickeners, such as carboxymethyl cellulose (CMC), carrageenan, or xanthan gum; any anionic polycarboxylate; any salts, such as sodium fluoride anticaries agents; and any sweeteners; the resultant mixture is agitated until a homogeneous gel phase is formed. Into the gel phase are added a pigment such as $TiO_2$, and any acid or base required to adjust the pH. These ingredients are mixed until a homogenous phase is obtained, whereupon the polishing agent/abrasive is mixed into the gel phase. The mixture is then transferred to a high speed/vacuum mixer; wherein, the inorganic thickener, such Sylodent 15; and surfactant ingredients are added to the mixture. Any water insoluble antibacterial agent, such as triclosan, are solubilized in the flavor oils and the solution is added to the mixture which is mixed at high speed for from 5 to 30 minutes, under vacuum of from about 20 to 50 mm of Hg, preferably about 30 mm Hg. The resultant product is in each case a homogeneous, semi-solid, extrudable paste or gel product.

The following example further describes and demonstrates preferred embodiments within the scope of the present invention. The example is given solely for illustration, and are not to be construed as limitation of this invention as many variations thereof are possible without departing from its spirit and scope.

EXAMPLE

Two hydrous silica dentifrice compositions of the present invention, designated Compositions 1 and 2 in Table I below, were prepared with a 20% total abrasive content as described below.

TABLE I

| Ingredients | Dentifrice Formulations | | |
|---|---|---|---|
| | Composition 1 | Composition 2 | Composition 3 |
| Deionized Water | 15.607 | 15.607 | 15.607 |
| Sodium Fluoride | 0.243 | 0.243 | 0.243 |
| Sodium Saccharin | 0.3 | 0.3 | 0.3 |
| Gantrez S-97 | 15.0 | 15.0 | 15.0 |
| Sodium Hydroxide (50%) | 1.2 | 1.2 | 1.2 |
| Sorbitol (70% Solution) | 20.85 | 20.85 | 20.85 |
| Titanium Dioxide | 1.0 | 1.0 | 1.0 |
| Glycerin | 20.0 | 20.0 | 20.0 |
| Sodium Carboxy-methyl Cellulose | 1.1 | 1.1 | 1.1 |
| Zeodent 165 Silica Thickener | 1.5 | 1.5 | 1.5 |
| Flavor Oils | 1.0 | 1.0 | 1.0 |
| Sodium Lauryl Sulfate | 1.5 | 1.5 | 1.5 |
| Triclosan | 0.3 | 0.3 | 0.3 |
| Zeodent 115 Silica Abrasive | 10.0 | 0.0 | 20.0 |
| Sylodent XWA300 Abrasive | 10.0 | 20.0 | 0.0 |

Compositions 1 and 2 were prepared in a jacketed, vacuum mixing tank at ambient room temperature. The glycerin and sorbitol humectants were added to the water in the mixing tank and agitation was started. The sodium fluoride salt, sodium saccharin sweetening agent, sodium carboxymethyl cellulose organic thickener, and Gantrez S-97 were added and mixing continued until a homogenous gel phase was obtained. Into the gel phase were added the $TiO_2$ pigment and the sodium hydroxide to adjust the pH. The Zeodent 165 silica thickening agent was then added to the abrasives, and the resulting mixture was added to the mixing tank under high agitation and a vacuum of about 30 mm of Hg. The triclosan was dissolved in the flavor oils to form a solution and the solution was added, with the sodium lauryl sulfate surfactant, to the mixing tank still maintaining the vacuum at about 30 mm of Hg. Mixing and vacuum continued for approximately 15 minutes. The resulting composition which was an extrudable paste, having a pH of about 7, was tubed.

The PCRs of Composition 1 and 2 were established using the modified Stookey procedure, as described above, and the results are recorded in Table II, below. RDA value for Composition 1 was determined by the method Hefferren method, as described about, and the results also recorded in Table II. Further, for purposes of comparison, the procedure of the Example was repeated using a dentifrice (designated Composition 3) having substantially the same composition; except, in Composition 3 the abrasive was an amorphous silica abrasive (Zeodent 115 Silica Abrasive). The PCR and RDA of comparative Composition 3 is also set forth in Table II, below.

TABLE II

PCR's of Dentifrice Formulations

| Composition | PCR Value | RDA Value |
|---|---|---|
| Composition 1 | 99.5 | 107 |
| Composition 2 | 105.0 | — |
| Composition 3 | 71.5 | 91 |

Referring to Table II, although Composition 1 containing both the silica hydrogel abrasive of the present invention and an amorphous silica abrasive exhibited a significantly higher (over 39%) PCR than comparative Composition 3, containing only the amorphous silica abrasive, the RDA value for Composition 1 was 107 and that for comparative Composition 3 was a relatively low 91, indicating that Composition 1 was moderately more abrasive than comparative Composition 3. Composition 2 containing as the sole abrasive the silica hydrogel of the present invention, exhibited a significantly higher PCR than both Composition 1 and comparative Composition 3.

What is claimed is:

1. A dentifrice composition, comprising:
   (a) an orally acceptable dentifrice vehicle from about 5% to about 95% by weight of the dentifrice composition; and
   (b) a silica hydrogel from about 3 to about 30% of the dentifrice composition, containing from 10 to 25% water by weight, wherein:
      (i) the silica hydrogel is composed of particles of from about 2 to about 4 microns, the particles having the properties;
      (ii) a BET surface area is in the range of 150 to 400 $m^2$/g of silica;
      (iii) an oil absorption is less than about 100 $cm^3$/100 g silica; and
      (iv) a pH, in a 5% w/w suspension of the silica in boiled ($CO_2$ free) demineralized water, equal to or greater than 8.5; and
   wherein, the dentifrice composition has an RDA of about 90 to about 250 and a PCR from about 70 to about 130.

2. A dentifrice composition according to claim 1, wherein said composition further comprises a fluoride ion source.

3. A dentifrice composition according to claim 2, further comprising a surfactant.

4. A dentifrice composition according to claim 3, wherein said composition has a pH above about 7 and wherein the surfactant is sodium lauryl sulfate.

5. A dentifrice composition according to claim 4, further comprising from about 5% to about 70% of a humectant selected from glycerin, sorbitol, propylene glycol and mixtures thereof.

6. A dentifrice composition according to claim 1, in the form of a toothpaste, tooth powder, prophylaxis paste, lozenge, gum, or oral gel.

7. A dentifrice composition according to claim 1, wherein the dentifrice composition contains an antitartar or an antibacterial agent or mixture thereof, and an anionic polycarboxylate.

8. A dentifrice composition according to claim 1, wherein the dentifrice composition has an RDA from about 95 to about 160.

9. A method for reducing stain and/or plaque and inhibiting gingivitis comprising the application of a safe and effective amount of a composition according to claim 1, to the teeth and other oral surfaces.

10. A method for reducing stain and/or plaque and inhibiting gingivitis comprising the application of a safe and effective amount of a composition according to claim 2, to the teeth and other oral surfaces.

* * * * *